United States Patent
Narimatsu et al.

(10) Patent No.: US 6,824,519 B2
(45) Date of Patent: Nov. 30, 2004

(54) HEART-SOUND DETECTING APPARATUS

(75) Inventors: Kiyoyuki Narimatsu, Komaki (JP); Toshihiko Ogura, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 481 days.

(21) Appl. No.: 09/942,864

(22) Filed: Aug. 31, 2001

(65) Prior Publication Data
US 2003/0004425 A1 Jan. 2, 2003

(30) Foreign Application Priority Data
Jun. 20, 2001 (JP) ...................................... 2001-186222

(51) Int. Cl.[7] .............................................. A61B 5/02
(52) U.S. Cl. ...................................... 600/528; 600/500
(58) Field of Search ................................ 600/528, 586, 600/490, 500–503

(56) References Cited

U.S. PATENT DOCUMENTS

| | | | | |
|---|---|---|---|---|
| 3,581,735 A | * | 6/1971 | Gentner et al. ............. | 600/528 |
| 3,985,121 A | * | 10/1976 | Hellenbrand ................ | 600/502 |
| 4,129,125 A | * | 12/1978 | Lester et al. ................ | 600/484 |
| 4,905,706 A | * | 3/1990 | Duff et al. .................. | 600/514 |
| 5,002,060 A | * | 3/1991 | Nedivi ....................... | 600/484 |
| 5,012,815 A | * | 5/1991 | Bennett et al. ............. | 600/528 |
| 5,025,809 A | * | 6/1991 | Johnson et al. ............. | 600/528 |
| 5,218,969 A | * | 6/1993 | Bredesen et al. ........... | 600/523 |
| 5,301,679 A | * | 4/1994 | Taylor ........................ | 600/586 |
| 5,557,681 A | | 9/1996 | Thomasson | |
| 5,860,933 A | * | 1/1999 | Don Michael ............. | 600/528 |
| 5,957,866 A | | 9/1999 | Shapiro et al. | |
| 6,279,871 B1 | | 8/2001 | Ogura | |
| 6,527,729 B1 | * | 3/2003 | Turcott ....................... | 600/528 |

FOREIGN PATENT DOCUMENTS

| | | |
|---|---|---|
| EP | 1 055 395 A2 | 11/2000 |
| EP | 1 095 611 A1 | 5/2001 |

* cited by examiner

Primary Examiner—Mark Bockelman
(74) Attorney, Agent, or Firm—Oliff & Berridge, PLC

(57) ABSTRACT

An apparatus for detecting a heart sound of a living subject, including a memory device which stores heart-sound characteristic information which is characteristic of a heart sound of the subject, a heart-sound sensor which is adapted to be worn on a body portion of the subject that is distant from a chest of the subject and which detects, from the body portion, a physical signal containing a heart-sound component and supplies the physical signal, and a heart-sound determining device for determining, based on the heart-sound characteristic information stored in the memory device, the heart-sound component contained in the physical signal.

11 Claims, 13 Drawing Sheets

I SOUND
II SOUND

HEART-SOUND DETECTING APPARATUS

BACKGROUND OF THE INVENTION

1. Field of Invention

The present invention relates to a heart-sound detecting apparatus and particularly to such an apparatus which detects a heart sound by extracting or determining, from a physical signal containing a heart-sound component, the heart-sound component.

2. Description of Related Art

Heart sounds are detected to make diagnosis of heart disease. In addition, heart sounds may be detected to determine, in combination with a pulse wave, a pulse-wave propagation velocity at which the pulse wave propagates through a living subject. In addition, since pulse-wave propagation velocity reflects arteriosclerosis which, in turn, directly relates to hypertension, it is desirable to measure, the velocity as part of a daily medical check at home.

In general, heart sounds are detected using a heart-sound microphone which is usually directly worn on the skin of a prescribed portion of the chest, e.g., right above the heart. A heart-sound signal provided by the heart-sound microphone worn on the chest has a great signal-to-noise (S/N) ratio. Thus, the heart-sound signal which is filtered by a standardized filter can directly be used to determine a reference point for making diagnosis or determining pulse-wave propagation velocity.

However, when the heart-sound microphone is used to detect heart sounds, the subject needs to take off their clothes and thereby expose the chest. Thus, it is considerably cumbersome to detect heart sounds using the heart-sound microphone. In particular, when pulse-wave propagation velocity is measured at home as part of a daily medical check, it is desirable to detect heart sounds in an easier manner.

In this background, it has been proposed to provide a heart-sound detecting apparatus which detects a heart sound at a position distant from the chest of a living subject, based on the fact that the heart sound is transmitted from the heart to that position. This apparatus is disclosed in U.S. Patent Application claming priority from Japanese Patent Application No. 2001-030879. This apparatus includes a pressure-pulse-wave sensor which is worn on an upper arm of a subject and extracts a heart-sound component from a pressure-pulse-wave signal supplied from the sensor.

However, the magnitude of the heart-sound component contained in the pressure-pulse-wave signal or physical signal detected from the upper arm distant from the chest is weak. The magnitude of the other signal components, such as physical sounds occurring to the upper arm, external noise, or artifact, is also strong. Therefore, in many cases, the signal filtered by the conventional, standardized filter may not be used to determine one or more reference points which are needed to make diagnosis or determine pulse-wave propagation velocity.

SUMMARY OF THE INVENTION

It is therefore an object of the present invention to provide a heart-sound detecting apparatus which can accurately determine a heart-sound component which is contained in a physical signal, even if the magnitude of the heart-sound component may be weak relative to the magnitude of the physical signal as a whole.

The Inventors have intensively studied about how to achieve the above-indicated object, and obtained the following findings. Usually, a heart-sound signal supplied by a heart-sound microphone is filtered by a filter having a considerably large frequency range. The heart-sound signal is filtered because there are great differences among respective heart-sound signals obtained from individual subjects. That is, the respective heart sounds of individual subjects may have largely different frequency ranges and/or waveforms. Hence, the Inventors have found that if a heart-sound frequency range and/or a heart-sound waveform of each individual subject are/is determined in advance as heart-sound characteristic information, a heart-sound component can be accurately determined based on the heart-sound characteristic information. The heart-sound component can be accurately determined from a physical signal actually detected from the each subject even if the magnitude of the heart-sound component may be weak relative to that of the physical signal as a whole. The present invention has been developed based on this finding.

The above object has been achieved by the present invention. According to a first feature of the present invention, there is provided an apparatus for detecting a heart sound of a living subject, comprising a memory device which stores heart-sound characteristic information which is characteristic of a heart sound of the subject, a pressure-pulse-wave sensor which is adapted to be worn on a limb of the subject, detects a pressure pulse wave which is produced from an artery of the limb and is propagated from the artery to the pressure-pulse-wave sensor, and produces a pressure-pulse-wave signal representing the detected pressure pulse wave and containing a heart-sound component; and a heart-sound determining means for determining, based on the heart-sound characteristic information stored in the memory device, the heart-sound component contained in the pressure-pulse-wave signal.

According to this feature, the memory device stores heart-sound characteristic information which is characteristic of a heart sound of the living subject, and the heart-sound determining means determines, based on the heart-sound characteristic information characteristic of the heart sound, the heart-sound component contained in the pressure-pulse-wave signal supplied by the pressure-pulse-wave sensor. Therefore, even if the magnitude of the heart-sound component may be weak relative to that of the physical signal as a whole, the present apparatus can accurately determine the heart-sound component.

According to a second feature of the present invention, the heart-sound characteristic information comprises a heart-sound microphone which is adapted to be worn on the chest of the subject and detects, in advance, the heart sound of the subject; and a heart-sound characteristic-information obtaining means for obtaining the heart-sound characteristic information from the heart sound detected in advance by the heart-sound microphone from the chest of the subject. The heart-sound characteristic-information obtaining means obtains the heart-sound characteristic information comprising a heart-sound frequency range consisting of a plurality of frequencies which are predetermined by subjecting, to a frequency analysis, the heart sound detected in advance by the heart-sound microphone from the chest of the subject. The heart-sound determining means comprises a first heart-sound determining means for extracting from the pressure-pulse-wave signal, the heart-sound component having the plurality of frequencies of the heart-sound frequency range.

According to this feature, the memory device stores the heart-sound frequency range which is predetermined based on the heart sound detected in advance from the chest of the subject and which is characteristic of the subject, and the heart-sound determining means extracts, from the pressure-pulse-wave signal supplied by the pressure-pulse-wave sensor, the heart-sound component having the frequencies of the heart-sound frequency range. Thus, even if the magnitude of the heart-sound component may be weak relative to that of the physical signal as a whole, the present apparatus can accurately extract the heart-sound component.

According to a third feature of the present invention, the heart-sound characteristic information comprises a heart-sound microphone which is adapted to be worn on the chest of the subject and detects, in advance, the heart sound of the subject, and a heart-sound-characteristic-information obtaining means for obtaining the heart-sound characteristic information from the heart sound detected in advance by the heart-sound microphone from the chest of the subject. The heart-sound-characteristic-information obtaining means obtains the heart-sound characteristic information comprising a first portion of the heart sound detected in advance by the heart-sound microphone from the chest of the subject, said first portion being detected during a predetermined time interval. The heart-sound determining means comprises a second heart-sound determining means for determining as the heart-sound component, a second portion of the pressure-pulse-wave signal supplied by the pressure-pulse-wave sensor, said second portion having a length corresponding to the predetermined time interval and having a waveform best approximating a waveform of said first portion of the heart sound.

According to this feature, the memory device stores, as the heart-sound, characteristic information characteristic of the subject, a portion of the heart sound which is detected in advance from the chest of the subject and which has a great signal-to-noise ratio. Since the heart-sound determining means determines, as the heart-sound component, a portion of the pressure-pulse-wave signal detected by the pressure-pulse-wave sensor that has a length corresponding to the predetermined time interval and has a waveform best approximating a waveform of the portion of the heart-sound signal stored in the memory device, the present apparatus can accurately determine the heart-sound component from the pressure-pulse-wave signal even if the magnitude of the heart-sound component contained in the pressure-pulse-wave signal may be weak.

According to a fourth feature of the present invention, the heart-sound characteristic information comprises a heart-sound microphone which is adapted to be worn on the chest of the subject and detects, in advance, the heart sound of the subject; and a heart-sound-characteristic-information obtaining means for obtaining the heart-sound characteristic information from the heart sound detected in advance by the heart-sound microphone from the chest of the subject. The heart-sound-characteristic-information obtaining means comprises a frequency-time analyzing means for subjecting, to a frequency-time analysis, the heart sound detected in advance by the heart-sound microphone from the chest of the subject, and thereby providing a frequency-time analyzed signal. The heart-sound-characteristic-information obtaining means obtains the heart-sound characteristic information comprising a first portion of the heart sound detected in advance by the heart-sound microphone from the chest of the subject, said first portion having a plurality of frequencies of a heart-sound frequency range which is predetermined based on the frequency-time analyzed signal provided by the frequency-time analyzing means, and being detected during a predetermined time interval. The heart-sound determining means comprises a first heart-sound determining means for extracting, from the pressure-pulse-wave signal, a signal component having the plurality of frequencies of the heart-sound frequency range; and a second heart-sound determining means for determining, as the heart-sound component, a second portion of the signal component extracted by the first heart-sound determining means, said second portion having the plurality of frequencies of the heart-sound frequency range, having a length corresponding to the predetermined time interval, and having a waveform best approximating a waveform of said first portion of the heart sound.

According to this feature, the memory device stores a portion of the heart sound, detected in advance from the chest of the subject, that has the frequencies of a heart-sound frequency range which is predetermined based on a frequency-time analyzed signal of the heart sound, and is detected during a predetermined time interval. The heart-sound determining means determines; as the heart-sound component, a portion of the signal component extracted by the first heart-sound determining means that has the frequencies of the heart-sound frequency range, has a length corresponding to the predetermined time interval, and has a waveform best approximating a waveform of the stored portion of the heart sound. Thus, the present apparatus can accurately determine the heart-sound component from the physical signal.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
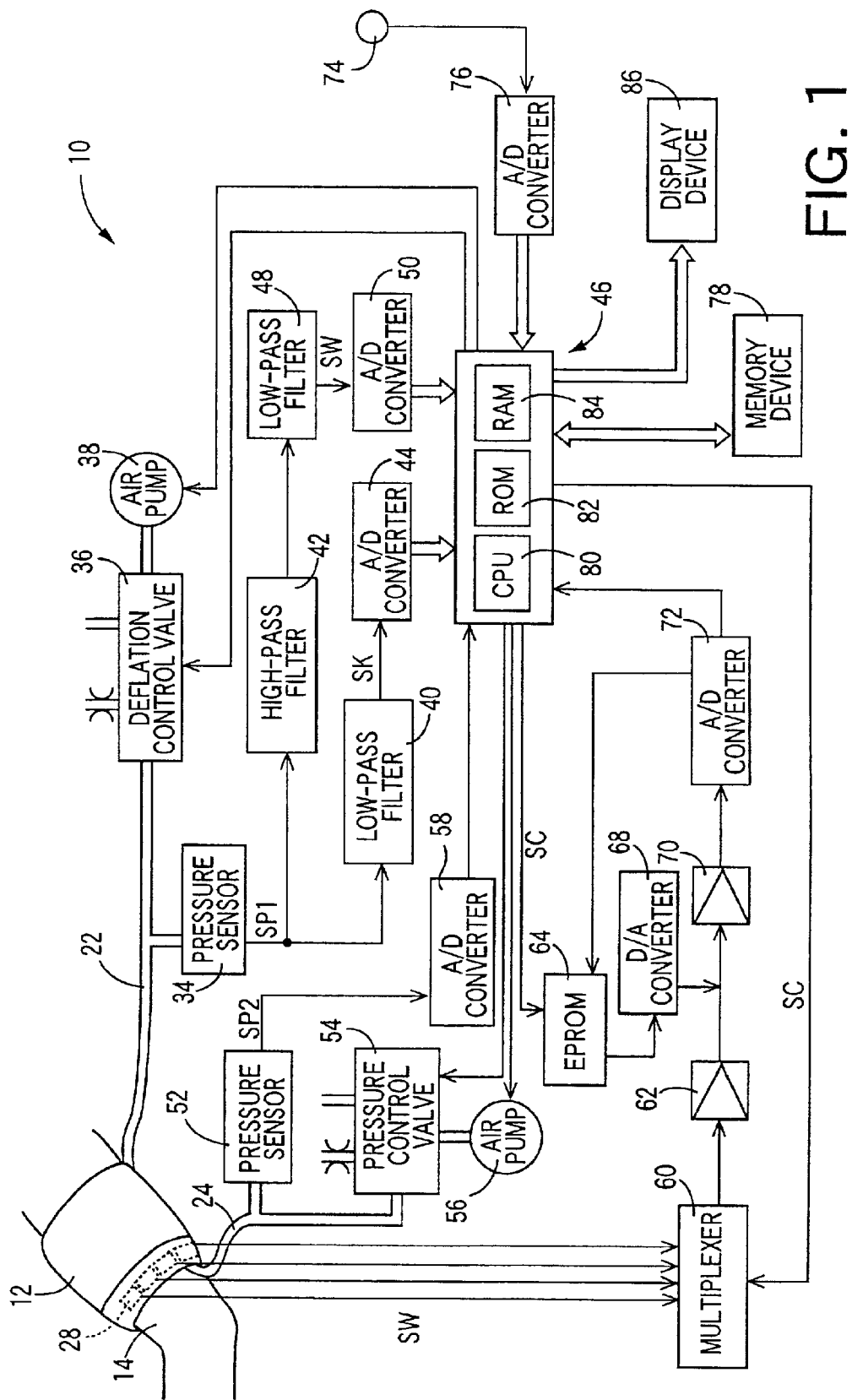
FIG. 1 is a diagrammatic view showing a construction of a pulse-wave-propagation-velocity measuring apparatus functioning as a heart-sound detecting apparatus, to which the present invention is applied.

Hereinafter, there will be described a preferred embodiment of the present invention in detail by reference to the accompanying drawings. FIG. 1 shows a diagrammatic view showing a construction of a pulse-wave-propagation-velocity measuring apparatus 10 functioning as a heart-sound detecting apparatus, to which the present invention is applied. The present apparatus 10 also functions as a blood-pressure measuring apparatus.

Figure 2:
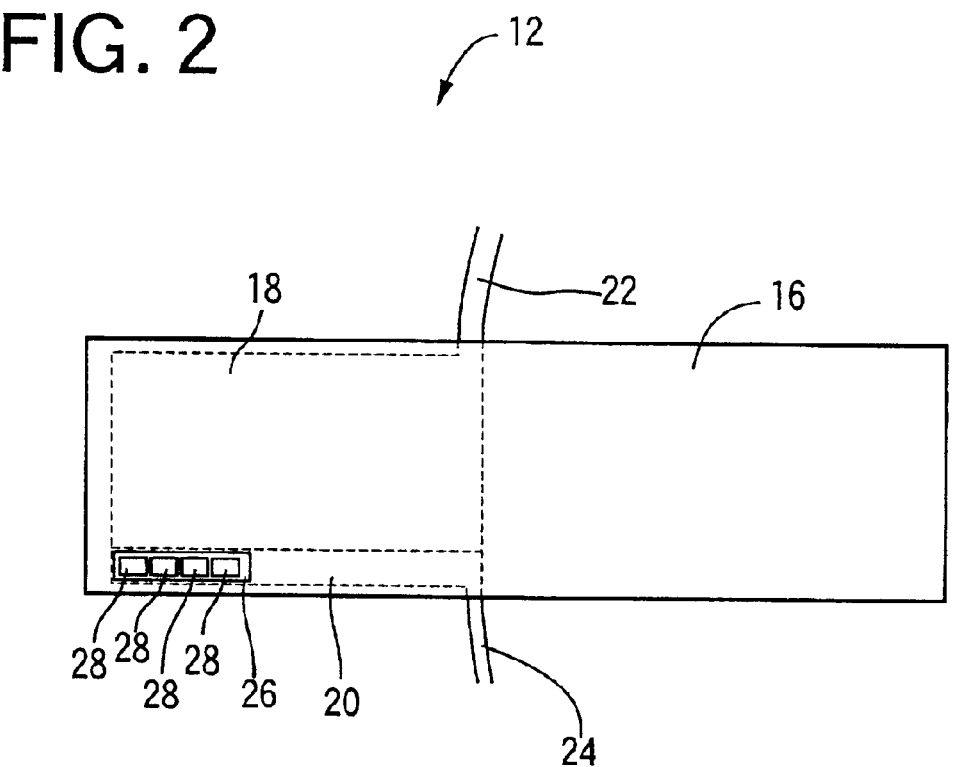
FIG. 2 is a development view of an inflatable cuff of the apparatus of FIG. 1.

In FIG. 1, reference numeral 12 designates an inflatable cuff which is adapted to be wound around a right upper arm 14 of a patient. FIG. 2 is a development view of the cuff 12. As shown in FIG. 2, the cuff 12 includes a belt-like cover bag 16 which is formed of a non-stretchable and considerably rigid cloth and has substantially the same length as that of a common inflatable cuff which is used to measure a blood pressure of an upper arm of a patient. However, a width of the cuff 12 is longer than that of the common cuff by a length corresponding to a width of a small cuff 20, described below.

In the cover bag 16, there are provided a large cuff 18 and the small cuff 20 each of which has substantially the same length (e.g., 24 cm) as that of a circumferential length of the upper arm 14 and is formed of rubber. The large cuff 18 has substantially the same width as that of a rubber bag employed in the common cuff. The width of the small cuff 20 is smaller than that of the large cuff 18 and is, for example, 2 cm. The large cuff 18 and the small cuff 20 are provided such that respective one long sides thereof are adjacent to each other. In a state in which the cuff 12 is wound around the upper arm 14, the small cuff 20 is positioned at a distal-side end of the cuff 12. The large cuff 18 and the small cuff 20 are connected to respective pipings 22, 24 for supplying pressurized air thereto.

A flexible support plate 26 which has substantially the same width as that of the small cuff 20 is fixed to an inner surface of the cuff 12 that contacts the upper arm 14 when the cuff 12 is wound around the same 14. More specifically described, the support plate 26 is fixed to a portion of the inner surface of the cuff 12 that corresponds to the small cuff 20. As such, when the cuff 12 is wound around the upper arm 14, the support plate 26 is pressed by the small cuff 20. The support plate 26 supports four pressure-pulse-wave sensors 28 such that the four sensors 28 are arranged along a straight line in a lengthwise direction of the plate 26. Between each pair of adjacent sensors 28, there is provided a considerably small space of 0.9 mm length. Each pressure-pulse-wave sensor 28 produces a pressure-pulse-wave signal SM containing not only a brachial-artery-pulse-wave component but also a heart-sound component. Thus, each pressure-pulse-wave sensor 28 also functions as a heart-sound sensor.

Figure 3:
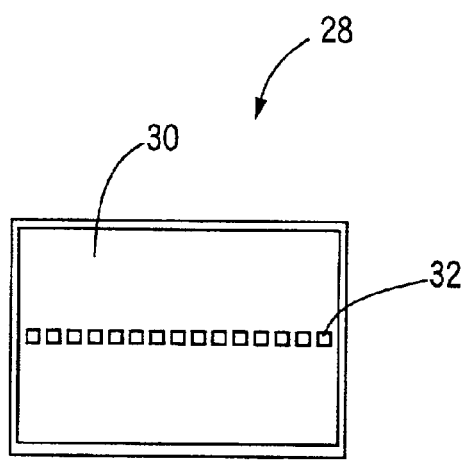
FIG. 3 is a plan view of a pressure-pulse-wave sensor of the apparatus of FIG. 1.

FIG. 3 is a plan view of one of the four pressure-pulse-wave sensors 28. The sensor 28 has a press surface 30 which is defined by a semiconductor chip such as monocrystalline silicon and has a length of about 13 mm in a lengthwise direction of the cuff 12 (i.e., in a left-right direction in FIG. 3). In the press surface 30, there are provided a number of semiconductor-based pressure sensing elements (or pressure detecting elements) 32 at a regular interval of distance along a straight line in the lengthwise direction of the cuff 12. In the present embodiment, each pressure-pulse-wave sensor 28 has fifteen pressure sensing elements 32 which are arranged at a regular spacing interval of 0.2 mm.

Back to FIG. 1, the large cuff 18 is connected to a pressure sensor 34, a deflation control valve 36, and an air pump 38 via the piping 22. The deflation control valve 36 is selectively placed in a pressure-supply position in which the control valve 36 permits a pressurized air to be supplied from the air pump 38 to the large cuff 18, a slow-deflation position in which the control valve 18 permits the pressurized air to be slowly discharged from the large cuff 18, and a quick-deflation position in which the control valve 36 permits the pressurized air to be quickly discharged from the large cuff 18.

The pressure sensor 34 detects an air pressure $PK_1$ in the large cuff 18, and supplies a first pressure signal $SP_1$ representing the detected pressure $PK_1$, to each of a low-pass filter 40 and a high-pass filter 42 via an amplifier, not shown. The low-pass filter 40 extracts, from the pressure signal $SP_1$, a static-pressure component contained in the signal $SP_1$, i.e., a cuff-pressure signal SK representing the pressing pressure of the large cuff 18. The cuff-pressure signal SK is supplied to a control device 46 via an A/D (analog-to-digital) converter 44. The high-pass filter 42 extracts; from the pressure signal $SP_1$, an alternating component having frequencies not lower than 0.8 Hz. The high-pass filter 42 also supplies the thus extracted alternating-component signal to a low-pass filter 48 via an amplifier, not shown. The low-pass filter 48 extracts; from the alternating-component signal supplied from the high-pass filter 42, an alternating component having frequencies not higher than 10.8 Hz. This alternating-component signal provides a cuff-pulse-wave signal SW representing the alternating component of the pressure signal $SP_1$. The cuff-pulse-wave signal SW is supplied to the control device 46 via an A/D converter 50.

The small cuff 20 is connected to a pressure sensor 52, a pressure control valve 54, and an air pump 56 via the piping 24. The pressure sensor 52 detects an air pressure $PK_2$ in the small cuff 20, and supplies a second pressure signal $SP_2$ representing the detected pressure $PK_2$, to the control device 46 via an A/D converter 50. The pressure control valve 54 changes the pressure of the pressurized air supplied from the air pump 56, and supplies the pressurized air having the thus changed pressure to the small cuff 20.

A multiplexer 60 sequentially supplies, according to a switch signal SC supplied from the control device 46, the respective pressure-pulse-wave signals SM supplied from the sixty pressure sensing elements 32 of the four pressure-pulse-wave sensors 28 to an amplifier 62. Each signal SM is for a prescribed time duration. An EPROM (erasable programmable ROM) 64 stores, for the sixty pressure sensing elements 32, respective correction signals for eliminating respective individual sensitivity differences among the pressure sensing elements 32. The EPROM 64 also sequentially supplies according to the switch signal SC supplied from the control device 46, i.e., in synchronism with the respective switching operations of the multiplexer 60, the respective correction signals; to a D/A (digital-to-analog) converter 68.

The correction signals are supplied in such a manner that the respective correction signals sequentially correspond to the respective pressure sensing elements 32 supplying the respective pressure-pulse-wave signals SM being currently dealt with by the multiplexer 60.

Each of the sixty pressure-pulse-wave signals SM that have been amplified by the amplifier 62 and a corresponding one of the sixty correction signals that have been converted to respective analog signals by the D/A converter 68 are supplied to an amplifier 70. Thus, the sixty corrected pressure-pulse-wave signals SM supplied to the amplifier 70 have a uniform sensitivity. Each of the sixty corrected pressure-pulse-wave signals SM is supplied to an I/O (input-and-output) port of the control device 46 via an A/D converter 72.

A heart-sound microphone 74 is adapted to be worn on a prescribed position on a skin of a chest of the living subject. The heart-sound microphone 74 detects heart sounds of the subject and supplies a heart-sound signal SH representing the detected heart sounds to the control device 46 via an A/D converter 76. A memory device 78 which may be provided by a RAM, a magnetic disc device (HDD), or a removable medium (MO, DVD, etc.) stores heart-sound-characteristic information, such as a heart-sound frequency range RF or a reference waveform, described later.

The control device 46 is provided by a so-called microcomputer including a CPU (central processing unit) 80, a ROM (read only memory) 82, and a RAM (random access memory) 84. The CPU 80 processes signals according to the control programs pre-stored in the ROM 82 by utilizing the temporary-storage function of the RAM 84. The CPU 80 controls the deflation control valve 36 and the air pump 38 to carry out a blood-measure measurement and controls the pressure control valve 54 and the air pump 56 to detect a pressure pulse wave. The CPU 80 also determines a blood-pressure value BP, extracts a heart sound, determines a pulse-wave-propagation velocity PWV, and controls a display device 86 to display the thus determined blood-pressure value BP and pulse-wave-propagation velocity PWV.

Figure 4:
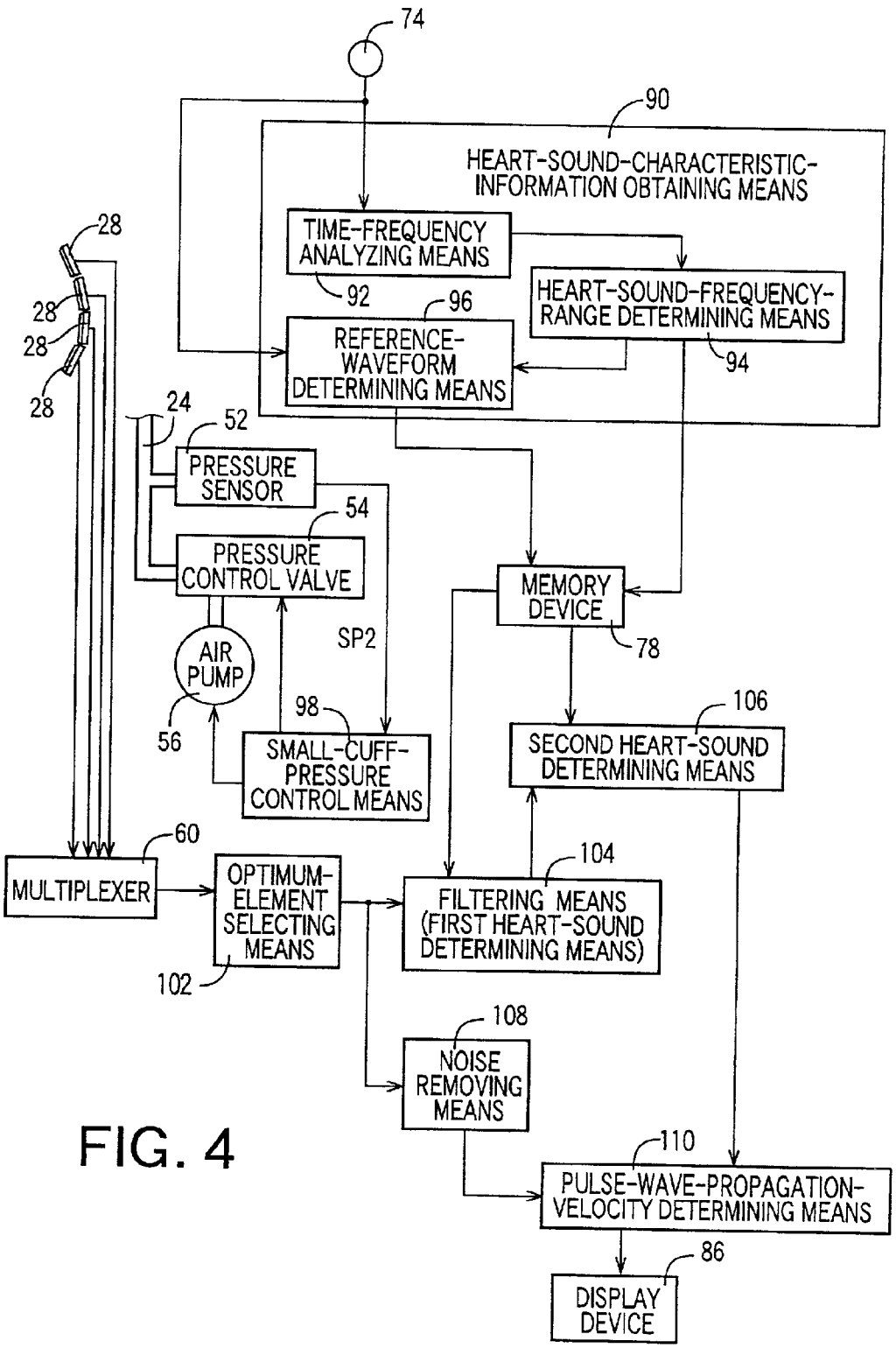
FIG. 4 is a block diagram for explaining essential functions of a control device of the apparatus of FIG. 1, including the functions of detecting a heart sound and determining, based on the detected heart sound, a pulse-wave propagation velocity.

FIG. 4 is a block diagram for explaining essential functions of the control device 46 of the pulse-wave-propagation-velocity measuring apparatus 10. In particular, the functions of detecting heart sounds and determining, based on the detected heart sounds, a pulse-wave-propagation velocity.

A heart-sound-characteristic-information obtaining means 90 includes a time-frequency analyzing means 92, a heart-sound-frequency range determining means 94, and a reference-waveform determining means 96. The time-frequency analyzing means 92 analyzes, with respect to time and frequency, the heart-sound signal SH supplied from the heart-sound microphone 74 (i.e., carries out a time-and-frequency analysis of the signal SH). The time-frequency analyzing means 92 simultaneously analyzes, with respect to both time and frequency, the heart-sound signal SH. Thus, the time-frequency analyzing means 92 provides a time-wise change of the frequency-analyzed magnitude values of the signal SH by utilizing, e.g., a wavelet transform, or a fast Fourier transform (FFT) as applied to each of prescribed time intervals.

Figure 5:
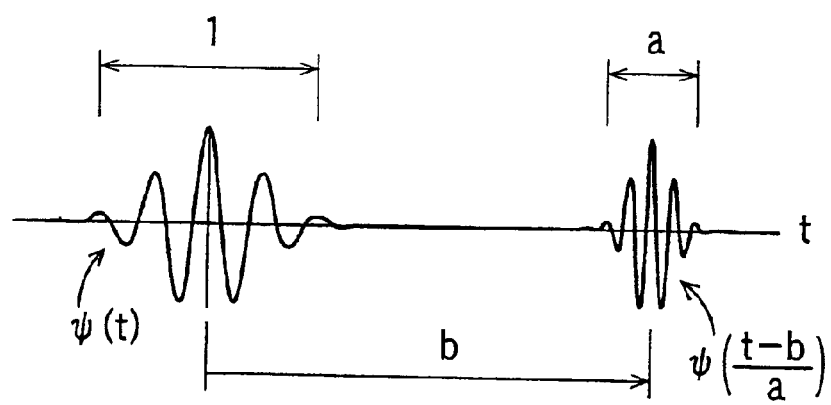
FIG. 5 is a graph showing a wavelet function.

The wavelet transform will be described below. A wavelet function, Ψ(t), shown in FIG. 5, is modified to a function Ψ((t−b)/a) of a translate parameter b to translate a waveform represented by the function Ψ(t) along a time axis t and a scale parameter a to expand or contract the width of the waveform represented by the function Ψ(t) along the time axis t. The wavelet transform is defined as a function of the parameters a, b that is obtained by integrating, with respect to the time t, the product of the thus modified wavelet function Ψ((t−b)/a) and a function f(t) representing the heart-sound signal SH. That is, the wavelet transform is defined by the following expression (1) pre-stored in the ROM 8:

$$W(b, 1/a) = \int_{-\infty}^{\infty} \frac{1}{\sqrt{|a|}} \overline{\Psi\left(\frac{t-b}{a}\right)} f(t) dt \quad (1)$$

Since the waveform represented by the modified wavelet function Ψ((t−b)/a) has a width scaled by the parameter a along the time axis t, a parameter 1/a indicates frequency. Since the waveform represented by the wavelet function Ψ((t−b)/a) is translated by the parameter b along the time axis t, the parameter b indicates time.

Figure 6A:
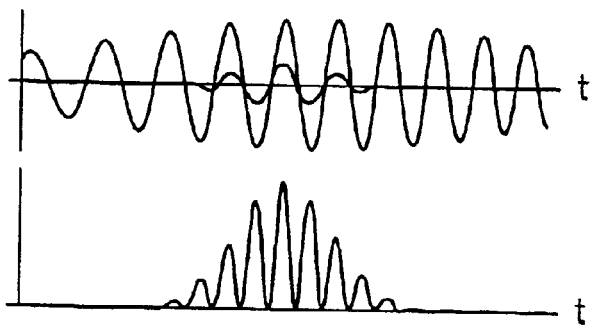
FIG. 6A is a graph showing a wavelet function $\Psi((t-b)/a)$ which approximates a portion of a certain function $g(t)$.
Figure 6B:
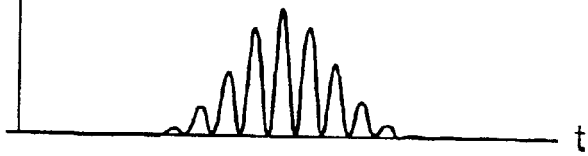
FIG. 6B is a graph showing the product of the wavelet function $\Psi((t-b)/a)$ and the function $g(t)$.
Figure 7A:
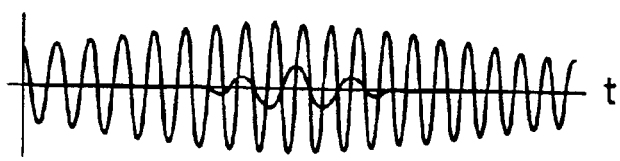
FIG. 7A is a graph showing the wavelet function $\Psi((t-b)/a)$ which does not approximates a portion of a certain function $h(t)$.
Figure 7B:
FIG. 7B is a graph showing the product of the wavelet function $\Psi((t-b)/a)$ and the function $h(t)$.

FIGS. 6A and 6B, and FIGS. 7A and 7B are graphs for explaining what is meant by the wavelet transform defined by the above expression (1). FIG. 6A shows that a wavelet function Ψ((t−b)/a) in which appropriate parameters a, b have been selected substantially approximates a portion of a certain function g(t). FIG. 7A shows that the wavelet function Ψ((t−b)/a) does not approximate any portion of a certain function h(t). FIG. 6B shows the product of the wavelet function Ψ((t−b)/a) and the function g(t) shown in FIG. 6A. FIG. 7B shows the product of the wavelet function Ψ((t−b)/a) and the function h(t) shown in FIG. 7A. In the case, shown in FIG. 6A, in which the wavelet function Ψ((t−b)/a) substantially approximates a portion of the function g(t), the plus or minus sign of the product of the wavelet function Ψ((t−b)/a) and the function g(t) does not change as the time t elapses. Therefore, a great value is obtained by integrating the product function. On the other hand, in the case shown in FIG. 7A, in which the wavelet function Ψ((t−b)/a) does not approximate any portions of the function h(t), the plus and minus sign of the product of the wavelet function Ψ((t−b)/a) and the function h(t) frequently changes from plus to minus and from minus to plus as the time t elapses. Therefore, only a small value is obtained by integrating the product function. Thus, the above-indicated expression (1) provides a great value when the parameters a, b are appropriately selected so that the wavelet function Ψ((t−b)/a) approximates a portion of the function f(t) representing the heart-sound signal SH. The expression (1) provides a small value when the wavelet function Ψ((t−b)/a) does not approximate any portions of the function f(t).

Figure 8A:
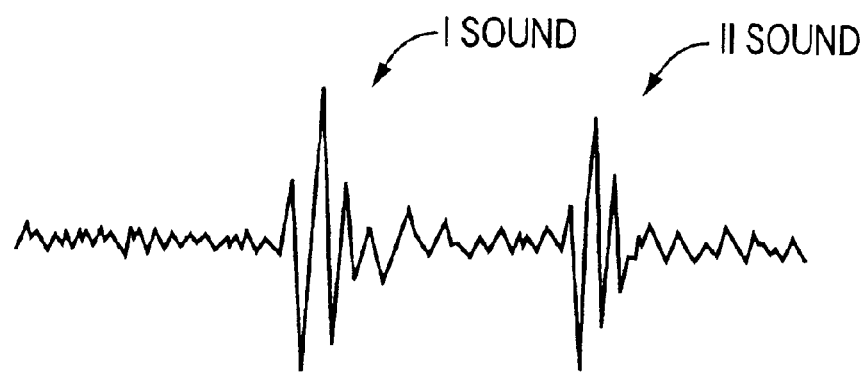
FIG. 8A is a graph showing a heart-sound signal SH which is supplied from a heart-sound microphone 74 of the apparatus of FIG. 1.
Figure 8B:
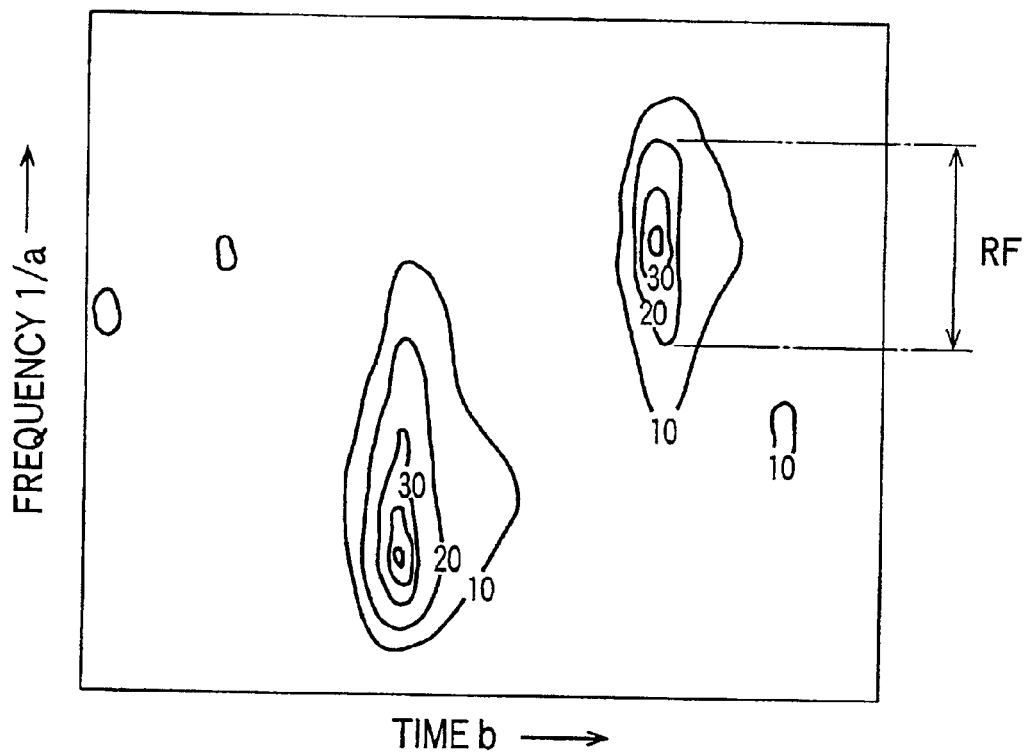
FIG. 8B is a graph showing a contour map which is obtained by subjecting the heart-sound signal SH shown in FIG. 8A, to a time-frequency analysis, i.e., a wavelet transform.

In the above-indicated expression (1), the scale parameter a corresponding to the frequency f and the translate parameter b corresponding to the time t are gradually changed. Each time at least one of the two parameters a, b is changed, an integral value is obtained from the wavelet transform, i.e., expression (1). FIG. 8A shows a waveform of the heart-sound signal SH supplied from the heat-sound microphone 74. FIG. 8B shows a three-dimensional graph (i.e., a contour map) that is obtained by analyzing the waveform of the heart-sound signal SH shown in FIG. 8A, with respect to time, frequency, and signal magnitude, by utilizing the wavelet transform, i.e., expression (1). In the contour map, three contour lines represent three integral values, i.e., 10, 20, and 30, respectively.

The fast Fourier transform transforms a signal (i.e., a two-dimensional signal with respect to time and signal magnitude) that is obtained from each of prescribed time intervals, into a different sort of two-dimensional signal with respect to frequency and signal magnitude. Therefore, if the function f(t) is subjected to the fast Fourier transform each time the time t is moved from one time interval to the next time interval, the function f(t) is transformed into a three-dimensional signal with respect to time, frequency, and signal magnitude like the contour map obtained by the wavelet transform.

The heart-sound-frequency-range determining means 94 determines, based on the three-dimensional graph obtained by the time-frequency analyzing means 92, a frequency range RF of the heart sounds represented by the heart-sound signal SH supplied from the microphone 74. The determining means 94 stores the thus determined heart-sound frequency range RF in the memory device 78. The heart-sound frequency range RF may be one which includes respective frequencies of all heart sounds including first and second heart sounds I, II. However, in the present embodiment, the heart-sound-frequency-range determining means 94 determines a frequency range including frequencies of a second heart sound II as part of the heart sounds. For example, regarding the three-dimensional graph shown in FIG. 8B, the heart-sound-frequency-range determining means 94 determines, as the heart-sound frequency range RF, a range of frequencies which correspond to respective times when the second heart sound II, shown in FIG. 8A, occur. The range of frequencies correspond to respective signal magnitudes not smaller than a reference value (e.g., 20). FIG. 8B shows the thus determined heart-sound frequency range RF. This heart-sound frequency range RF is characteristic of the subject.

The reference-waveform determining means 96 extracts, from a portion of the heart-sound signal SH that was detected in a prescribed time interval, a signal component having the frequencies of the heart-sound frequency range RF determined by the heart-sound-frequency-range determining means 94. The reference-wave form determining means 96 also determines a waveform of the thus extracted component as a reference waveform. In addition, the reference-waveform determining means 96 determines a prescribed periodic point on the thus determined reference waveform as a reference point. The thus determined reference waveform and point in the memory device 78 is then stored. The reference waveform is also characteristic of the subject. The above-indicated time interval is so prescribed as to include a time or a time interval which is necessary for making a diagnosis. Since, in the present apparatus 10, a pulse-wave-propagation-velocity determining means 110, described later, needs a starting point of a second heart sound II, the prescribed time interval includes the starting point of second heart sound II. The prescribed periodic point means the starting point of second heart sound II.

A small-cuff-pressure control means 98 controls, based on the second pressure signal $SP_2$ supplied from the pressure sensor 52, the pressure control valve 54 and the air pump 56 to increase the air pressure $PK_2$ in the small cuff 20 up to a prescribed target pressure $PM_2$ and then keep the pressure $PK_2$ at the target pressure $PM_2$. The target pressure $PM_2$ is prescribed at such a value which assures that the press surface 30 which is provided on the inner surface of the cuff 12 and to which the pressure-pulse-wave sensors 28 are fixed, is pressed against the upper arm 14. The flow of blood is not occluded through a brachial artery 100 of the upper arm 14.

Figure 9:
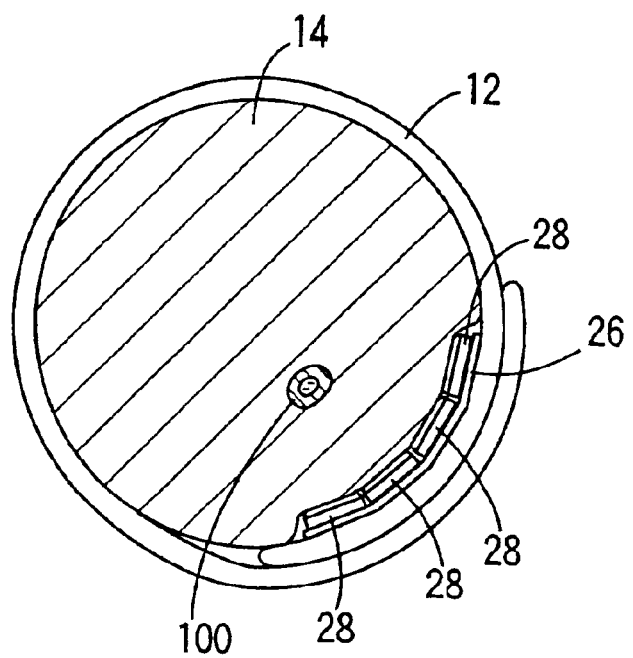
FIG. 9 is a cross-section view for explaining a state in which the cuff is wound around an upper arm of a living subject.
Figure 10:
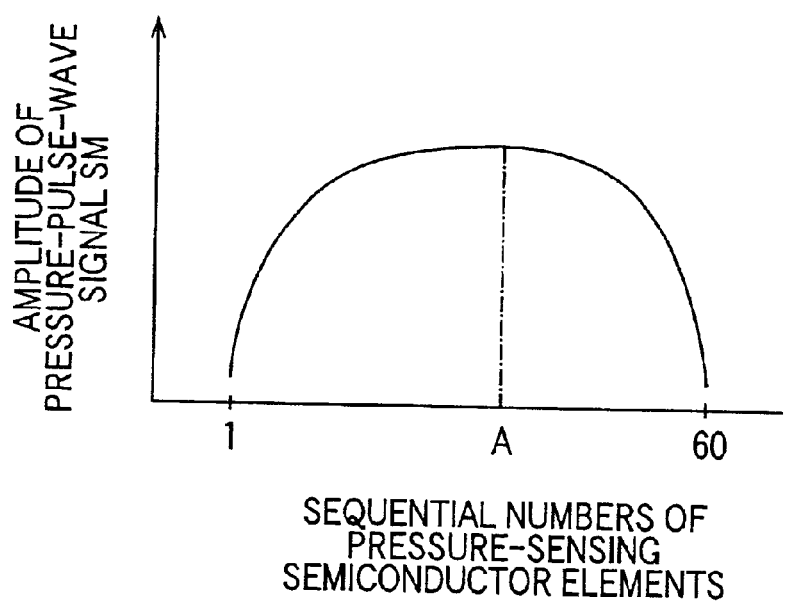
FIG. 10 is a graph showing a relationship between individual pressure-sensing semiconductor elements and respective amplitudes of respective pressure-pulse-wave signals SM generated by the individual pressure-sensing elements.

An optimum-element selecting means 102 selects, from the sixty pressure-sensing semiconductor elements 32 of the four pressure-pulse-wave sensors 28, an optimum pressure-sensing element 32 that is the most appropriate to detect heart sounds (hereinafter, referred to as the optimum element A). FIG. 9 is a cross-section view showing the state in which the cuff 12 is wound around the upper arm 14. As shown in FIG. 9, the pressure-sensing elements 32 provided on the press surfaces 30 of the pressure-pulse-wave sensors 28 have respective different distances from the brachial artery 100 of the upper arm 14. Therefore, it is desirable that one of the pressure-sensing elements 32 that is located right above, or in the vicinity of, the brachial artery 100 be selected as the optimum element A. The optimum element A can detect, with the highest sensitivity, the pressure pulse wave. FIG. 10 shows a relationship between the pressure-sensing elements 32 and respective amplitudes of the pressure-pulse-wave signals SM detected by the elements 32. In the figure, the sequential numbers of the pressure-sensing elements 32 start with one of opposite ends of the array of elements 32 provided on the press surfaces 30. Respective amplitudes of pressure-pulse-wave signals SM detected by nearer pressure-sensing elements 32 to the brachial artery 100 are greater than those detected by remoter elements 32 from the artery 100. Therefore, the optimum-element selecting means 102 selects, as the optimum element A, one of the pressure-sensing elements 32 that provides a pressure-pulse-wave signal SM having a greater amplitude in the relationship shown in FIG. 10. Most preferably, the element 32 that provides the signal SM having the greatest amplitude.

A filtering means 104 as a first heart-sound determining means, i.e., a first portion of a heart-sound determining means, subjects the pressure-pulse-wave signal SM supplied from the optimum element A to a digital filter. This allows, based on the heart-sound frequency range RF stored in the memory device 78, only a signal component having frequencies falling in the frequency range RF to pass therethrough. Thus, the filtering means 104 extracts, from the pressure-pulse-wave signal SM, only the signal component having the frequencies falling in the frequency range of the second heart sound II whose level is considerably low in the signal SM.

A second heart-sound determining means 106 as a second portion of the heart-sound determining means determines a time interval in which a waveform of the signal component extracted by the filtering means 104 best approximates the reference waveform stored in the memory device 78. Since the reference waveform is determined based on the second heart sound II, a portion of the pressure-pulse-wave signal SM that occurs in the time interval determined by the second heart-sound determining means 106 corresponds to the second heart sound II. In addition, in a state in which the waveform of the signal component extracted by the filtering means 104 best approximates the reference waveform, the second heart-sound determining means 106 determines a time point corresponding to the starting point of the second heart sound H as the reference waveform. This time point indicates a time when the starting point of second heart sound II contained in the pressure-pulse-wave signal SM occurs. The method in which the second heart-sound determining means 106 determines the time interval in which the waveform of the signal component extracted by the filtering means 104 best approximates the reference waveform, may be to obtain a cross-correlation function. The cross-correlation function is obtained with respect to the waveform of the signal component extracted by the filtering means 104 and the reference waveform. Second heart-sound determining means 106 determines as the above-indicated time interval, a time interval corresponding to the reference waveform in a state in which the cross-correlation function takes a maximal value.

Figure 11:
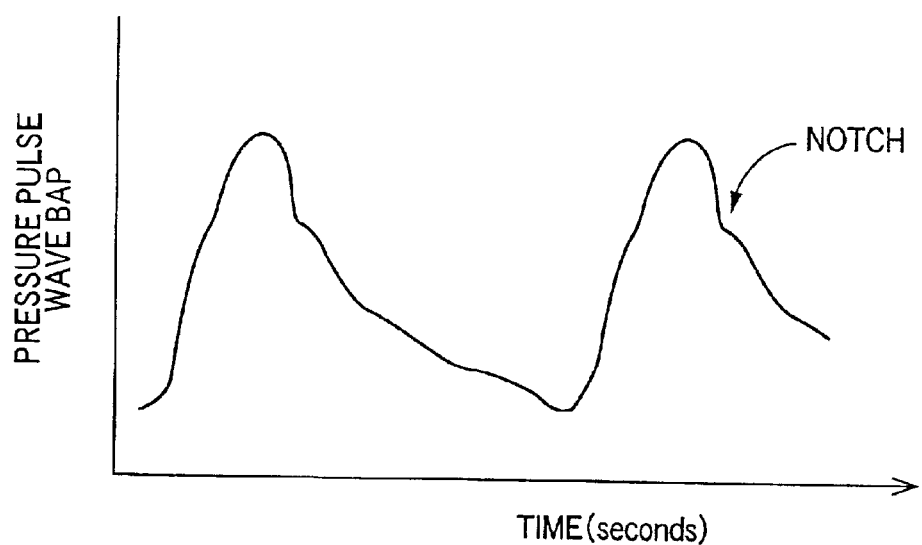
FIG. 11 is a graph showing a pressure pulse wave BAP from which noise has been extracted by a noise removing means.

A noise removing means 108 subjects the pressure-pulse-wave signal SM supplied from the optimum element A to a digital filter. The digital filter thereby removes noise from the signal SM so as to extract the pressure pulse wave BAP produced when the brachial artery 100 pulsates. Since the pressure pulse wave BAP is a heartbeat-synchronous wave, the noise removing means 108 removes, from the signal SM, a component having frequencies not lower than 50 Hz. FIG. 11 shows a pressure pulse wave BAP which is freed of noise by the noise removing means 108.

The pulse-wave-propagation-velocity determining means 110 determines a timing when the rising point of second heart sound II determined by the second heart-sound determining means 106 is detected, a timing when a notch of the pressure pulse wave BAP that corresponds to the second heart sound II is detected, and determines a time difference between the two timings. The pressure pulse wave BAP has been freed of noise by the noise removing means 108. The thus determined time difference is determined as a pulse-wave propagation time DT (sec) that is needed for the pressure pulse wave BAP to propagate from the aortic valve of the heart to a portion of the brachial artery 100 that is located right below the pressure-pulse-wave sensors 28. The pulse-wave-propagation-velocity determining means 110 determines, based on the thus determined pulse-wave propagation time DT, a pulse-wave propagation velocity PWV (m/sec), according to the following expression (2), pre-stored in the ROM 76:

$$PWV=L/DT \quad (2)$$

The thus determined pulse-wave propagation velocity PWV is displayed on the display device 86. In the above expression (1), L is a length of an artery from an initial end of the aorta to a portion thereof located right below the optimum element A, and is obtained in advance by experiments.

Figure 12:
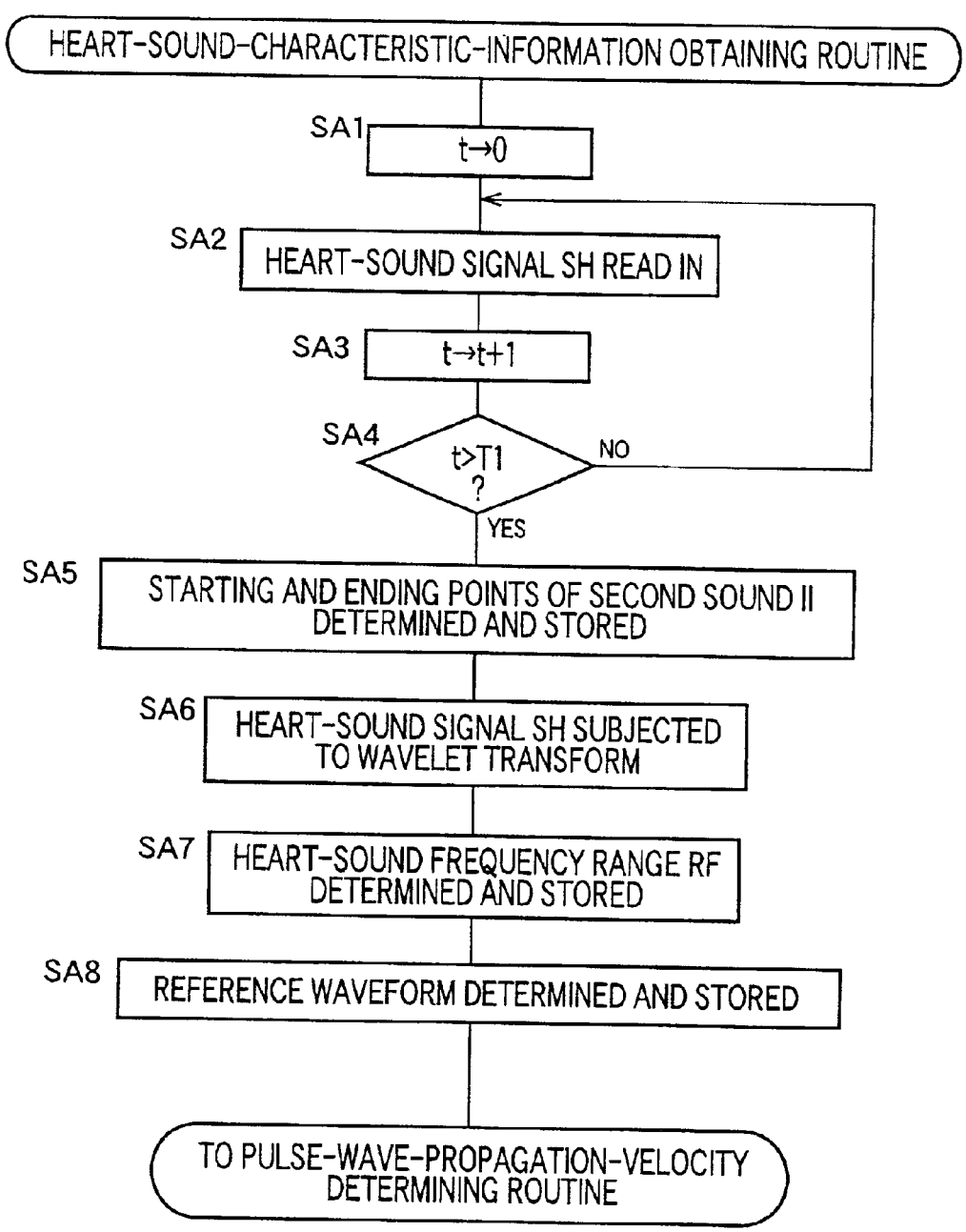
FIG. 12 is a flow chart representing a control program according to which the control device of FIG. 4 operates for obtaining heart-sound-characteristic information.
Figure 13:
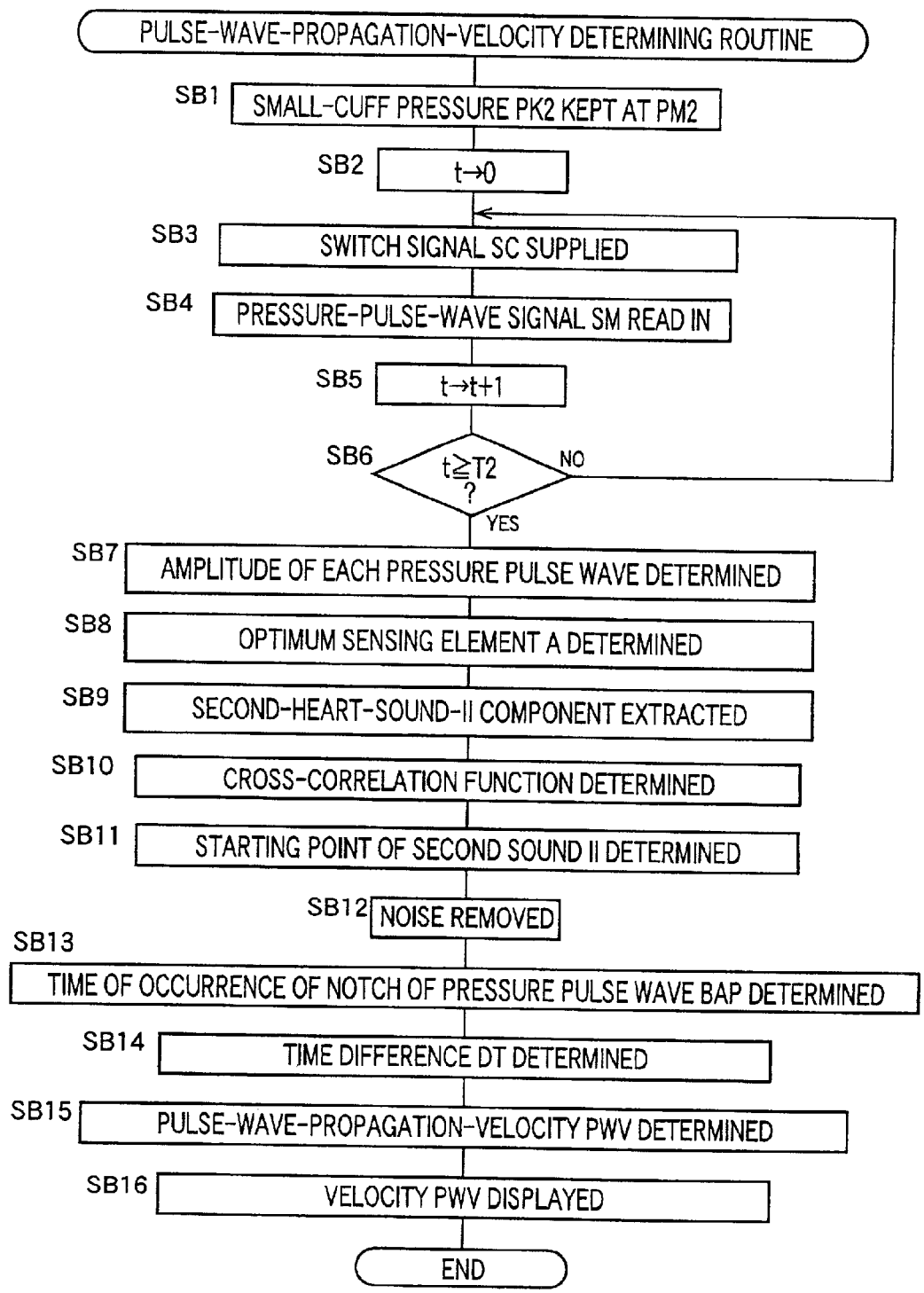
FIG. 13 is a flow chart representing a control program according to which the control device of FIG. 4 operates for determining a pulse-wave propagation velocity.

FIGS. 12 and 13 are flow charts representing respective control programs according to which the control device 46 is operated. The flow chart of FIG. 12 represents a heart-sound-characteristic-information obtaining routine, and the flow chart of FIG. 13 represents a pulse-wave-propagation-velocity determining routine.

First, there will be described the heart-sound-characteristic-information obtaining routine shown in FIG. 12. This routine is carried out before the routine shown in FIG. 13 is carried out. When the routine of FIG. 12 is carried out, it is needed to wear the heart-sound microphone 74 on the chest of a patient, but it is not needed to wear the cuff 12 on the upper arm 14.

First, at Step SA1 (hereinafter, "Step" is omitted), the control device 46 resets a number counted by a timer t, to zero. Next, at SA2, the control device 46 reads in the heart-sound signal SH supplied from the heart-sound microphone 74. At SA3, the control device 46 adds one to the number counted by the timer. At SA4, the control device 46 judges whether a time represented by the number counted by the timer t has exceeded a prescribed read-in time $T_1$ corresponding to an average pulse period, i.e., an inverse of an average pulse rate. While negative judgments are made at SA4, Steps SA2 to SA4 are repeated to continue reading in the heart-sound signal SH. Since the heart-sound signal SH is supplied from the heart-sound microphone 74 worn on the chest, the signal SH has a greater signal-to-noise (S/N) ratio than that of the pressure-pulse-wave signal SM supplied from each pressure-pulse-wave sensor 28 worn on the upper arm 14. The S/N ratio of the signal SM is defined as a ratio of the heart-sound component thereof to the remaining components thereof as noise.

Meanwhile, if a positive judgment is made at SA4, the control proceeds with Steps SA5 and SA6 corresponding to the heart-sound-characteristic-information obtaining means 90. At SA5, the control device 46 determines, based on the heart-sound signal SH read while Steps SA2 to SA4 are repeated, a starting point and an ending point of a second heart sound II. The control device 46 uses a known technique (so-called "smoothing energy curve") which is widely employed to determine characteristic points of heart sounds. The respective positions of the starting and ending points and the respective times of detection of the starting and ending points are stored in the memory device 78.

Next, the control goes to SA6 corresponding to the time-frequency analyzing means 92. At SA6, the heart-sound signal SH read in while Steps SA2 to SA4 are repeated is subjected to the wavelet transform. Thus, a time-frequency analyzed signal is obtained as a contour map as shown in FIG. 8B.

Then, the control goes to SA7 corresponding to the heart-sound-frequency-range determining means 94. At SA7, the control device 46 determines, as a heart-sound frequency range RF characteristic of a second heart sound II of the subject, a range of respective frequencies. The range of respective frequencies correspond to respective times between the starting and ending points determined at SA5 on the time-frequency analyzed signal obtained at SA6. The respective frequencies correspond to respective signal magnitudes not smaller than a reference value. The thus determined heart-sound frequency range RF is stored in the memory device 78.

Next, the control goes to SA8 corresponding to the reference-waveform determining means 96. At SA8, the control device 46 extracts a signal component having the frequencies of the heart-sound frequency range RF determined at SA7 and determines a waveform of the thus extracted components as a reference waveform. The signal component is extracted from a portion of the heart-sound signal SH, obtained at Steps SA2 to SA4, that occurs between the starting and ending points of the second heart sound II, determined at SA5. This reference waveform is stored in the memory device 78. Though the heart-sound signal SH read in at SA2 has a considerably great S/N ratio, the signal component extracted at SA2 is obtained by removing noise from the portion of the signal SH that occurs between the starting and ending points of second heart sound II.

Next, there will be described the pulse-wave-propagation-velocity determining routine shown in FIG. 13. This routine is carried out in a state in which the upper arm 14 is not pressed by the large cuff 18.

In FIG. 13, first, at Step SB1 corresponding to the small-cuff-pressure control means 98, the control device 46 starts the air pump 56 and operates the pressure control valve 54. The pressing pressure $P_{K2}$ of the small cuff 20 is thus kept at a considerably low pressure of, e.g., 40 mmHg.

Next, at SB2, a number counted by a timer t is replaced with "0", so that the timer t is reset to zero. At SB3, the control device 46 outputs the switch signal SC to switch the multiplexer 60 and the EPROM 64 at a period sufficiently shorter than an average pulse period. Then, at SB4, the control device 46 reads in the pressure-pulse-wave signal SM supplied from the multiplexer 60.

Next, at SB5, the control device 46 adds one to the number counted by the timer t. At SB6, the control device 46 judges whether a time indicated by the number counted by the timer t has exceeded a prescribed read-in period $T_2$. Like the read-in time $T_1$, the read-in period $T_2$ may be equal to an average pulse period, i.e., a length of one average heartbeat-synchronous pulse. Each time one switch signal SC is supplied to the multiplexer 60 at SB3, one of the respective pressure-pulse-wave signals SM detected by the sixty pressure-sensing elements 32 is supplied from the multiplexer 60 to the control device 46. While Steps SB3 to SB6 are repeated sixty times, all the signals SM detected by the sixty elements 32 are supplied from the multiplexer 60 to the control device 46.

Next, the control goes to SB7 and SB8 corresponding to the optimum-element selecting means 102. First, at SB7, the control device 46 determines respective amplitudes of the respective pressure-pulse-wave signals SM which have been read in while Steps SB3 to S6 are repeated. At S8, the control device 46 determines the greatest one of the respective amplitudes determined at SB7. The control device 46 also determines, as the optimum element A, one of the pressure-sensing elements 32 that provides the greatest amplitude.

Next, the control goes to SB9 corresponding to the filtering means 104. At SB9, the control device 46 extracts, a signal component having frequencies falling in the heart-sound frequency range RF stored at SA7 in FIG. 12. The signal component is extracted from the pressure-pulse-wave signal SM supplied from the optimum element A selected at SB8. The signal component extracted from the pressure-pulse-wave signal SM has the frequencies of the second heart sound II of the subject.

Subsequently, the control goes to Steps SB10 and SB11 corresponding to the second heart-sound determining means 106. At SB10, the control device 46 determines a cross-correlation function with respect to the waveform of the signal component extracted at SB9 and the reference waveform stored at SA8 in FIG. 12. At SB11, the control device 46 determines a position of the reference waveform relative to the waveform extracted at SB9 in a state in which the cross-correlation function takes a maximal value. The control device 46 also determines, as a time of occurrence of a starting point of the second heart sound II as the extracted waveform, a time corresponding to a position of the starting point of the second heart sound II on the extracted waveform that corresponds to the starting point of the second heart sound II determined and stored at SA5 in FIG. 12.

Next, the control goes to SB12 corresponding to the noise removing means 108. More specifically described, at S8, the control device 46 subjects the pressure-pulse-wave signal SM detected by the optimum element A to a digital filter, so as to remove a signal component having frequencies not lower than 50 Hz. Thus, the pressure pulse wave BAP is extracted from the pressure-pulse-wave signal SM. Next, at SB13, the control device 46 determines, based on the pressure pulse wave BAP extracted at SB12, a time of occurrence of a notch (FIG. 11) to the pressure pulse wave BAP that corresponds to the starting point of second heart sound II.

Then, the control goes to Steps SB14, SB15 and SB16 corresponding to the pulse-wave-propagation-velocity determining means 110. At SB14, the control device 46 determines a pulse-wave propagation time DT between the time of occurrence of the starting point of the second heart sound II determined at SB11 and the time of occurrence of the notch of the pressure pulse wave BAP determined at SB13. Next, at SB15, the control device 46 determines a pulse-wave propagation velocity PWV by replacing the parameter DT of the expression (2) with the time difference DT determined at SB14. Next, at SB16, the thus determined pulse-wave propagation velocity PWV is displayed on the display device 86.

In the illustrated embodiment, the memory device 78 stores the two pieces of heart-sound characteristic information which is characteristic of the heart-sound signal SH of the living subject, i.e., the heart-sound frequency range RF and the reference waveform. At Steps SB10 and SB11 (the second heart-sound determining means 106), the starting point of the second heart sound II is determined, based on the reference waveform characteristic of the subject, on the pressure-pulse-wave signal SM supplied from the pressure-pulse-wave sensor 28. Thus, even if the magnitude of the heart-sound component is weak relative to that of the signal SM as a whole, the starting point of second heart sound II can be determined with accuracy.

More specifically described, in the illustrated embodiment, the heart-sound frequency range RF characteristic of the subject, determined based on the heart-sound signal SH obtained in advance from the chest of the subject, is stored in the memory device 78: at SA7. The component having the frequencies falling in the heart-sound frequency range RF is also extracted from the pressure-pulse-wave signal SM supplied from the pressure-pulse-wave sensor 28 at SB9 (the filtering means, i.e., the first heart-sound determining means 104). Since the reference waveform stored in the memory device 78, i.e., the second-heart-sound-II component from its starting point to its ending point is one which has been measured from the chest of the subject, the component has a great S/N ratio. Yet, the component is characteristic of the subject. Moreover, at Steps SB10 and SB11 (the second heart-sound determining means 106), a waveform of a portion of the signal extracted at SB9 that best approximates the reference waveform is determined as the second heart sound II. Thus, an accurate heart-sound signal can be obtained from the pressure-pulse-wave signal SM.

While the present invention has been described in its preferred embodiment by reference to the drawings, it is to be understood that the invention may otherwise be embodied.

For example, in the illustrated apparatus 10, the memory device 78 stores the heart-sound characteristic information which is obtained from the heart-sound signal SH produced by the heart-sound microphone 74. However, in the case where the memory device 78 is externally accessible to delete the information stored therein and store new information therein, it is possible to employ a separate device which measures a heart sound of a living subject, obtains heart-sound characteristic information from the measured heart sound, and stores the thus obtained heart-sound characteristic information in the memory device 78. In the latter case, the apparatus 10 may not employ the heart-sound microphone 74.

In addition, in the illustrated apparatus 10, the heart-sound signal SH is subjected to the time-frequency analysis, and the thus obtained time-frequency-analyzed signal is used to determine the heart-sound frequency range RF and the reference waveform. The filtering means (the first heart-sound determining means) 104 extracts, from the pressure-pulse-wave signal SM, the component having the frequencies falling in the heart-sound frequency range RF. The second heart-sound determining means 106 determines, as a second heart sound II, a portion of the extracted signal that best approximates the reference waveform. However, either one of the first and second heart-sound determining means 104, 106 can be omitted. More specifically described, since the component that is extracted from the pressure-pulse-wave signal SM and has the frequencies falling in the heart-sound frequency range RF is a sort of heart-sound signal extracted from a physical signal, the second means 106 may be omitted. Alternatively, the filtering means 104 may not be employed to extract, from the pressure-pulse-wave signal SM, the component having the frequencies falling in the heart-sound frequency range RF. The second means 106 may be adapted to directly compare the pressure-pulse-wave signal SM with the reference waveform and determine, as a second heart sound II, a portion of the signal SM that best approximates the reference waveform.

It is to be understood that the present invention may be embodied with other changes, improvements and modifications that may occur to a person skilled in the art without departing from the spirit and scope of the invention defined in the appended claims.

What is claimed is:

1. An apparatus for detecting a heart sound of a living subject, comprising:
    a memory device which stores heart-sound characteristic information which is characteristic of a heart sound of the subject;
    a pressure-pulse-wave sensor which is adapted to be worn on a limb of the subject, detects a pressure pulse wave which is produced from an artery of the limb and is propagated from the artery to the pressure-pulse-wave sensor, and produces a pressure-pulse-wave signal representing the detected pressure pulse wave and containing a heart-sound component; and
    a heart-sound determining means for determining, based on the heart-sound characteristic information stored in the memory device, the heart-sound component contained in the pressure-pulse-wave signal.

2. An apparatus according to claim 1, further comprising:
    a heart-sound microphone which is adapted to be worn on a chest of the subject and detects, in advance, the heart sound of the subject; and
    a heart-sound characteristic-information obtaining means for obtaining the heart-sound characteristic information from the heart sound detected in advance by the heart-sound microphone from the chest of the subject, wherein:
        the heart-sound characteristic-information obtaining means obtains the heart-sound characteristic information comprising a heart-sound frequency range consisting of a plurality of frequencies which are predetermined by subjecting, to a frequency analysis, the heart sound detected in advance by the heart-sound microphone from the chest of the subject, and
        the heart-sound determining means comprises a first heart-sound determining means for extracting from the pressure-pulse-wave signal, the heart-sound component having the plurality of frequencies of the heart-sound frequency range.

3. An apparatus according to claim 2, further comprising:
    a frequency-time analyzing means for subjecting, to a frequency-time analysis, the heart sound detected in advance by the heart-sound microphone from the chest of the subject, and thereby providing a frequency-time analysis signal; and
    a heart-sound-frequency-range determining means for determining the heart-sound frequency range based on the frequency-time analyzed signal provided by the frequency-time analyzing means.

4. An apparatus according to claim 1, further comprising:
    a heart-sound microphone which is adapted to be worn on a chest of the subject and detects, in advance, the heart sound of the subject; and
    a heart-sound-characteristic-information obtaining means for obtaining the heart-sound characteristic information from the heart sound detected in advance by the heart-sound microphone from the chest of the subject, wherein:
        the heart-sound-characteristic-information obtaining means obtains the heart-sound characteristic information comprising a first portion of the heart sound detected in advance by the heart-sound microphone from the chest of the subject, said first portion being detected during a predetermined time interval, and
        the heart-sound determining means comprises a second heart-sound determining means for determining, as the heart-sound component, a second portion of the pressure-pulse-wave signal supplied by the pressure-pulse-wave sensor, said second portion having a length corresponding to the predetermined time interval and having a waveform best approximating a waveform of said first portion of the heart sound.

5. An apparatus according to claim 4, further comprising:
    a waveform determining means for determining, from the heart sound detected in advance by the heart-sound microphone from the chest of the subject, the waveform of said first portion which is detected during the time interval between a first predetermined periodic point of the heart sound and a second predetermined periodic point thereof.

6. An apparatus according to claim 1, further comprising:
    a heart-sound microphone which is adapted to be worn on a chest of the subject and detects, in advance, the heart sound of the subject; and
    a heart-sound-characteristic-information obtaining means for obtaining the heart-sound characteristic information from the heart sound detected in advance by the heart-sound microphone from the chest of the subject, wherein:
        the heart-sound-characteristic-information obtaining means comprises a frequency-time analyzing means for subjecting, to a frequency-time analysis, the heart sound detected in advance by the heart-sound microphone from the chest of the subject, and thereby providing a frequency-time analyzed signal,
        the heart-sound-characteristic-information obtaining means obtains the heart-sound characteristic information comprising a first portion of the heart sound detected in advance by the heart-sound microphone from the chest of the subject, said first portion having a plurality of frequencies of a heart-sound frequency range which is predetermined based on the frequency-time analyzed signal provided by the frequency-time analyzing means, and being detected during a predetermined time interval, and
        the heart-sound determining means comprises:
            a first heart-sound determining means for extracting, from the pressure-pulse-wave signal, a signal component having the plurality of frequencies of the heart-sound frequency range, and
            a second heart-sound determining means for determining, as the heart-sound component, a second portion of the signal component extracted by the first heart-sound determining means, said second portion having the plurality of frequencies of the heart-sound frequency range, having a length corresponding to the predetermined time interval, and having a waveform best approximating a waveform of said first portion of the heart sound.

7. An apparatus according to claim 1, further comprising:
a heart-sound microphone which is adapted to be worn on a chest of the subject and detects, in advance, the heart sound of the subject; and
a heart-sound-characteristic-information obtaining means for obtaining the heart-sound characteristic information from the heart sound detected in advance by the heart-sound microphone from the chest of the subject.

8. An apparatus according to claim 7, wherein the heart-sound-characteristic-information obtaining means comprises a frequency-time analyzing means for subjecting, to a frequency-time analysis, the heart sound detected in advance by the heart-sound microphone from the chest of the subject, and thereby providing a frequency-time analyzed signal.

9. An apparatus according to claim 8, wherein the heart-sound-characteristic-information obtaining means further comprises a heart-sound-frequency-range determining means for determining, from the frequency-time analyzed signal, a heart-sound frequency range consisting of a plurality of frequencies corresponding to a plurality of signal magnitudes which are greater than a reference value, the heart-sound frequency range providing the heart-sound characteristic information.

10. An apparatus according to claim 9, wherein the heart-sound-characteristic-information obtaining means further comprises a waveform determining means for determining, as the heart-sound characteristic information, a waveform of a first portion of the heart sound detected in advance from the chest of the subject, said first portion having the plurality of frequencies of the heart-sound frequency range, and being detected during a time interval between a first predetermined periodic point of the heart sound and a second predetermined periodic point thereof.

11. An apparatus according to claim 1, wherein:
the heart-sound determining means determines, as the heart-sound component, a second heart sound of the subject, and
the apparatus further comprises a pulse-wave-propagation-velocity determining means for (a) determining a first timing when the second heart sound is detected by the pressure-pulse-wave sensor, and a second timing when a notch of the pressure pulse wave that corresponds to the second heart sound is detected by the pressure-pulse-wave sensor, (b) determining a time difference of the first and second timings, and (c) determining, based on the determined time difference, a pulse-wave propagation velocity at which the pressure pulse wave is propagated from a heart of the subject to the limb of the subject.

* * * * *

UNITED STATES PATENT AND TRADEMARK OFFICE
CERTIFICATE OF CORRECTION

PATENT NO. : 6,824,519 B2
DATED : November 30, 2004
INVENTOR(S) : Narimatsu et al.

It is certified that error appears in the above-identified patent and that said Letters Patent is hereby corrected as shown below:

Title page,
Item [56], References Cited, U.S. PATENT DOCUMENTS, should read

| | | | | | |
|---|---|---|---|---|---|
| -- | 2002/0107450 | A1 | 08/2002 | Ogura | |
| | 3,581,736 | A | * 06/1971 | Genther et al. | 600/528 |
| | 3,985,121 | A | * 10/1976 | Hellenbrand | 600/502 |
| | 4,129,125 | A | * 12/1978 | Lester et al. | 600/484 |
| | 4,905,706 | A | * 03/1990 | Duff et al. | 600/514 |
| | 5,002,060 | A | * 03/1991 | Nedivi | 600/484 |
| | 5,012,815 | A | * 05/1991 | Bennett et al. | 600/528 |
| | 5,025,809 | A | * 06/1991 | Johnson et al. | 600/528 |
| | 5,218,969 | A | * 06/1993 | Bredesen et al. | 600/523 |
| | 5,301,679 | A | * 04/1994 | Taylor | 600/586 |
| | 5,557,681 | A | 09/1996 | Thomasson. | |
| | 5,860,933 | A | * 01/1999 | Don Michael | 600/528 |
| | 5,957,866 | A | 09/1999 | Shapiro et al. | |
| | 6,527,729 | B1 | * 03/2003 | Turcott | 600/528 -- |

FOREIGN PATENT DOCUMENTS, insert
-- EP    1 055 395    A2    11/2000
   EP    1 095 611    A1    05/2001 --

Signed and Sealed this

Twenty-sixth Day of April, 2005

JON W. DUDAS
*Director of the United States Patent and Trademark Office*